US00PP11820P2

(12) United States Plant Patent
Cain

(10) Patent No.: US PP11,820 P2
(45) Date of Patent: Mar. 27, 2001

(54) GRAPE PLANT NAMED 'SUGRAEIGHTEEN'

(75) Inventor: David W. Cain, Bakersfield, CA (US)

(73) Assignee: Sun World International Inc., Bakersfield, CA (US)

( * ) Notice: Subject to any disclaimer, the term of this patent is extended or adjusted under 35 U.S.C. 154(b) by 0 days.

(21) Appl. No.: 09/196,839

(22) Filed: Nov. 20, 1998

(51) Int. Cl.[7] ..... A01H 5/00
(52) U.S. Cl. ..... Plt./207
(58) Field of Search ..... Plt./207

(56) References Cited

U.S. PATENT DOCUMENTS

| | | | |
|---|---|---|---|
| P.P. 5,151 | 12/1983 | Hahn et al. | Plt./207 |
| P.P. 7,377 | 11/1990 | Antclif | Plt./205 |
| P.P. 9,039 | 1/1995 | Larson | Plt./205 |
| P.P. 9,040 | 1/1995 | Larson | Plt./205 |

*Primary Examiner*—Howard J. Locker
*Assistant Examiner*—Melissa L. Kimball
(74) *Attorney, Agent, or Firm*—Knobbe Martens Olson & Bear LLP

(57) ABSTRACT

A new and distinct grapevine variety that possesses large, white, seedless berries having a desirable, distinctive, muscat flavor; crisp, juicy flesh; and tender skin.

1 Drawing Sheet

BACKGROUND AND SUMMARY OF THE INVENTION

This invention relates to the discovery and asexual propagation of a new variety of grapevine, *Vitis vinifera* cv. 'Sugraeighteen.' The new variety was first hybridized by David W. Cain in Wasco, Kern County, Calif., the variety being originated by controlled hybridization and subsequent ovule culture from normally abortive seeds. The new variety is characterized by its large, white, seedless berries having a desirable, distinctive, muscat flavor; crisp, juicy flesh; and tender skin.

The seed parent is the 'Redglobe' variety (U.S. Plant Pat. No. 4,787) and the pollen parent is an unnamed seedling 069-172, which arose from a cross between the 'Muscat Alexandria' variety (unpatented) and the 'Sugraone' variety (U.S. Plant Pat. No. 3,106). The parent varieties were first crossed in May, 1990, with the date of first flowering of the new variety being May, 1992. The new 'Sugraeighteen' variety was first asexually propagated by David W. Cain in Dec., 1992, in Wasco, Kern County, Calif., using cuttings.

The new grapevine variety cv. 'Sugraeighteen' most nearly resembles the 'Italia' grapevine variety. It differs from the 'Italia' variety (unpatented) by having more nearly round berries and by possessing rudimentary seeds that are not noticeable when eaten as opposed to normal, full size, lignified seeds of the 'Italia.'

'Sugraeighteen' differs from the 'Sugraone', 'Perlette' (unpatented), and 'Thompson Seedless' (unpatented) varieties and other commonly grown white seedless grapevine varieties by possessing a distinct and moderately strong muscat flavor somewhat similar to that of the 'Italia' grapevine variety. It also differs from the above listed varieties by having much more nearly round berries than 'Sugraone' or 'Thompson Seedless' and by having much larger natural berry size than either the 'Perlette' or 'Thompson Seedless' varieties and by being more responsive to exogenous gibberellic acid applications than either 'Sugraone' or 'Perlette.' The new variety retains very high productivity when spur pruned.

The new 'Sugraeighteen' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine.

DETAILED BOTANICAL DESCRIPTION OF THE INVENTION

Figure 1:
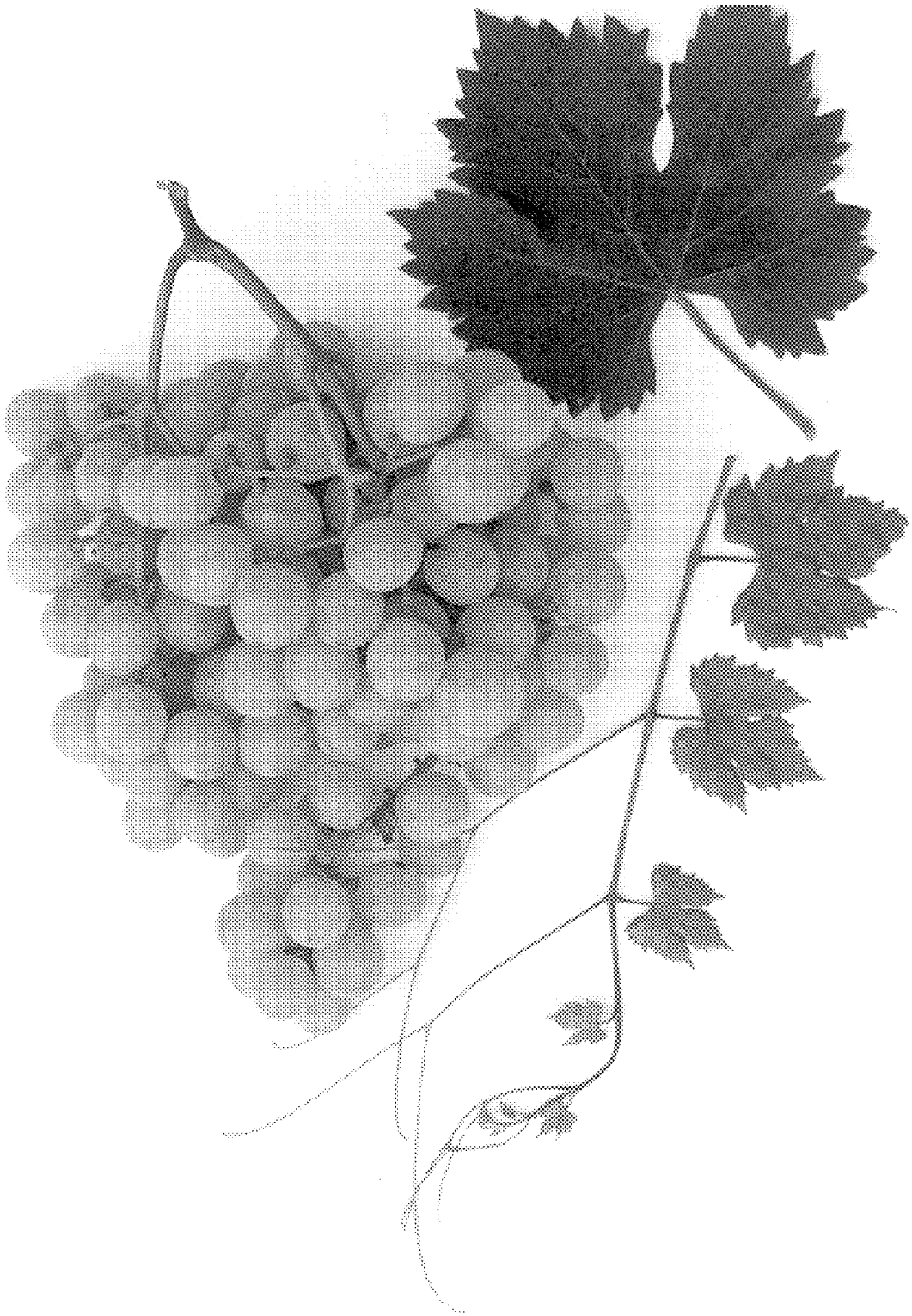

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugraeighteen' plants grown in the vicinity of Wasco, Kern County, Calif., during 1998, and is believed to apply to plants of the variety grown under similar conditions of soil and climate elsewhere:

VINE

General:
- *Size.*—Large.
- *Vigor.*—Vigorous.
- *Density of foliage.*—Very dense.
- *Productivity.*—Very productive, up to 28 Kg/vine spur fruitful.
- *Root stock.*—Own root.

Trunk:
- *Shape.*—Medium.
- *Straps.*—Long, split.
- *Surface texture.*—Shaggy.
- *Inner bark color.*—About Greyed-Orange 177C.

SHOOTS

Young shoot:
*Form of tip.*—Half-open.
*Distribution of anthocyanin coloration of tip.*—Piping.
*Intensity of anthocyanin coloration of tip.*—Weak to medium.
*Density of prostrate hairs on tip.*—Medium to dense.
*Density of erect hairs on tip.*—Absent to very sparse.

Flowering shoot:
*Vigor during flowering.*—Strong.
*Attitude during flowering on shoots which are not tied.*—Horizontal.
*Color of dorsal side of internodes.*—About Yellow-Green 144A with Greyed-Purple 183B stripes.
*Color of ventral side of internodes.*—About Yellow-Green 144A.
*Color of dorsal side of nodes.*—About Yellow-Green 144A with Greyed-Purple 183B stripes.
*Color of ventral side of nodes.*—About Yellow-Green 144A.
*Density of erect hairs on nodes.*—None.
*Erect hairs on internode.*—Absent.
*Density of prostrate hairs on nodes.*—None.
*Density of prostrate hairs on internodes.*—Absent.
*Anthocyanin coloration of buds.*—Absent or very weak.

Tendrils:
*Distribution on the shoot at full flowering.*—Discontinuous.
*Thickness.*—Thin.
*Color.*—About Yellow-Green 144B.
*Form.*—Mainly trifurcated.
*Number of consecutive tendrils.*—Up to two.
*Length of tendril.*—Very long, about 34.1 cm.

LEAVES

Young leaves:
*Color of upper surface of first 4 distal unfolded leaves.*—About Yellow-Green 146A with bronze spots.
*Average intensity of anthocyanin coloration of six distal leaves prior to flowering.*—Weak.
*Density of prostrate hairs between veins at lower surface of 4th distal unfolded leaf.*—Absent or very sparse.
*Erect hairs between veins at lower surface of 4th distal unfolded leaf.*—Absent.
*Density of prostrate hairs on veins at lower surface of 4th distal unfolded leaf.*—Sparse.
*Density of erect hairs on veins at lower surface of 4th distal unfolded leaf.*—Medium.

Mature leaves:
*Average length.*—About 12.7 cm.
*Average width.*—About 15.8 cm.
*Size of blade.*—Medium.
*Shape of blade.*—Pentagonal.
*Number of lobes.*—3.
*Anthocyanin coloration of main veins on the upper side of the blade.*—Absent.
*Mature leaf profile.*—Flat.
*Blistering surface of blade upper surface.*—Weak.
*Leaf blade tip.*—In the plane of the leaf.
*Undulation of margin.*—Slight.
*Apex.*—Acuminate.
*Thickness.*—Medium.
*Undulation of blade between main and lateral veins.*—Absent.
*Shape of teeth.*—Both sides convex.
*Length of teeth.*—Medium.
*Ratio length/width of teeth.*—Small.
*General shape of petiole sinus.*—Half open.
*Tooth at petiole sinus.*—Absent.
*Petiole sinus limited by veins.*—Absent.
*Shape of upper lateral sinus.*—Closed.
*Depth of upper lateral sinus.*—Shallow.
*Prostrate hairs between veins on lower surface of blade.*—Absent.
*Erect hairs between veins on lower surface of blade.*—Absent.
*Density of prostrate hairs on main veins on lower surface of blade.*—Sparse.
*Density of erect hairs on veins on lower surface of blade.*—Sparse.
*Prostrate hairs on main veins on upper surface of blade.*—Absent.
*Autumn coloration of leaves.*—About Yellow-Orange 15C.

Upper surface:
*Color.*—About Green 139A.
*Surface texture.*—Smooth.
*Surface appearance.*—Semi-glossy.
*Goffering of blade.*—Present.

Lower surface:
*Color.*—About Green 139B.
*Anthocyanin coloration of main veins on lower leaf surface.*—Absent.
*Glossiness.*—Medium.
*Pubescence.*—Absent.
*Surface texture.*—Smooth.
*Surface appearance.*—Semi-glossy.

Petiole:
*Length of petiole.*—Long, about 13.6 cm.
*Length of petiole compared to middle vein.*—Slightly longer.
*Prostrate hairs on petiole.*—None.
*Erect hairs on petiole.*—None.
*Shape of base of petiole sinus.*—V-shaped.

Woody shoot:
*Shape.*—Stocky.
*Internode length.*—Medium, about 11.7 cm.
*Width at node.*—About 20.6 mm.
*Cross section.*—Circular.
*Surface.*—Smooth.
*Main color.*—About Greyed-Orange 167C.
*Lenticels.*—Inconspicuous.
*Erect hairs on nodes.* —None.
*Erect hairs on internodes.*—None.
*Growth of axillary shoots.*—Very strong, about 74.6 cm.

Buds:
*Shape.*—Slightly pointed.
*Size.*—Medium, about 7.2×6.8 mm (length×width).
*Position.*—Slightly held out, about 35° angle.
*Cane bud fruitfulness.*—Basal most fruitful.
*Time of bud burst.*—Medium.

FLOWERS

General:
*Flower sex.*—Perfect.
*Length of first inflorescence.*—Medium to long, about 23.5 cm.

*Position of first flowering node.*—3rd.
*Number of inflorescences per shoot.*—1.1 to 2.
*Date of full bloom.*—May 23, 1998.
*Duration of bloom period.*—Average, about 10 days.
*Time of bloom.*—Medium, as compared with similar varieties in the growing area of Wasco, Kern County, Calif.
*Size* (*diameter of fully open flower*).—Medium.
*Color.*—About Yellow-Green, 145B.

FRUIT

General:
*Ripening period.*—Medium; about 10 days after the 'Thompson Seedless' variety.
*Date of ripening.*—Normally about August 10; varies from July 10 to as late as August 20, depending upon the year.
*Use.*—Fresh market.
*Keeping quality.*—Medium.
*Resistance.*—Insects: Good. Diseases: Good.
*Shipping quality.*—Medium.
*Date of first harvest.*—Aug. 20, 1998.
*Solids-sugar.*—Low (~15%) (taken Sep. 14, 1998).
*Refractometer test.*—About 15.0° brix.
*Acid.*—Very low; about 0.41 g/L tartaric acid.
*Juice pH.*—3.99.

Cluster:
*Bunch size* (*peduncle excluded*).—Medium to large.
*Bunch length* (*peduncle excluded*).—Long, about 23.5 cm.
*Bunch width.*—About 15.5 cm.
*Bunch weight.*—High, about 713.6 g (average).
*Bunch density.*—Medium.
*Number of berries.*—About 144.
*Form.*—Conical.

Peduncle:
*Length of peduncle.*—Medium, about 6.7 cm.
*Lignification of peduncle.*—Medium.
*Color.*—About Green 143C.

Berry:
*Size.*—Medium to large.
*Uniformity of size.*—Variable.
*Berry weight.*—Medium; natural weight averages about 5.4 g; can attain an average of about 11.5 g when plant is girdled and treated with gibberellic acid.
*Shape.*—Round.
*Presence of seeds.*—Rudimentary, about 2.9 mg/seed dry weight.
*Cross section.*—Circular.
*Dimensions.*—Longitudinal axis about 22.3 mm; horizontal axis about 20.4 mm.
*Skin color* (*without bloom*).—About Yellow-Green 145B.
*Juiciness of flesh.*—Very juicy.
*Berry firmness.*—Medium.
*Particular flavor.*—Mild to moderate musky muscat, similar to the 'Italia' variety.
*Bloom* (*cuticular wax*).—Medium.
*Pedicel length.*—Intermediate, about 6.6 mm.
*Berry separation from pedicel.*—Medium.
*Visibility of hilum.*—Slightly clear.
*Torus.*—Large, resembling the 'Redglobe' variety.

Skin:
*Thickness.*—Thin.
*Texture.*—Tender.
*Reticulation.*—Absent.
*Roughness.*—Absent.
*Tenacity.*—*Tenacious to flesh.*
*Tendency to crack.*—Tendency to crack at stylar end in some years.

What is claimed is:

1. A new and distinct variety of grapevine cv. 'Sugraeighteen' as herein illustrated and described.

* * * * *